US010973529B2

(12) United States Patent
Lavallee et al.

(10) Patent No.: US 10,973,529 B2
(45) Date of Patent: Apr. 13, 2021

(54) PATIENT-SPECIFIC SURGICAL GUIDE

(71) Applicant: ORTHOTAXY, La Tronche (FR)

(72) Inventors: Stephane Lavallee, St Martin d'Uriage (FR); Nicolas Demanget, Fontaine (FR); Jean-Michel Poirier, Grenoble (FR)

(73) Assignee: MINMAXMEDICAL, La Tronche (FR)

( * ) Notice: Subject to any disclaimer, the term of this patent is extended or adjusted under 35 U.S.C. 154(b) by 105 days.

(21) Appl. No.: 15/566,605

(22) PCT Filed: Apr. 18, 2016

(86) PCT No.: PCT/EP2016/058545
§ 371 (c)(1),
(2) Date: Oct. 13, 2017

(87) PCT Pub. No.: WO2016/166372
PCT Pub. Date: Oct. 20, 2016

(65) Prior Publication Data
US 2018/0085133 A1 Mar. 29, 2018

(30) Foreign Application Priority Data

Apr. 16, 2015 (EP) ..................................... 15305575

(51) Int. Cl.
*A61B 17/15* (2006.01)
*A61B 17/17* (2006.01)
(Continued)

(52) U.S. Cl.
CPC ............ *A61B 17/152* (2013.01); *A61B 17/15* (2013.01); *A61B 17/157* (2013.01);
(Continued)

(58) Field of Classification Search
CPC ..... A61B 17/15; A61B 17/152; A61B 17/157; A61B 17/17
See application file for complete search history.

(56) References Cited

U.S. PATENT DOCUMENTS 5,304,181 A  4/1994 Caspari et al.
5,601,563 A  2/1997 Burke et al.
(Continued)

FOREIGN PATENT DOCUMENTS

EP  2856951     *  4/2015
EP  2856951 A1     4/2015
(Continued)

OTHER PUBLICATIONS

Partial European Search Report issued for EP Patent Application No. 15305575.1, dated Nov. 16, 2015, 7 pages.
(Continued)

*Primary Examiner* — Christopher J Beccia
(74) *Attorney, Agent, or Firm* — Womble Bond Dickinson (US) LLP

(57) ABSTRACT

A patient-specific surgical guide including at least one guiding element for guiding a surgical instrument to treat a subcutaneous anatomical structure of the patient. A first patient-specific contact element with a first patient-specific contact surface to fit a portion of the subcutaneous anatomical structure is rigidly connected to the at least one guiding element. The patient-specific surgical guide includes at least one second patient-specific contact element having at least one support element for supporting a percutaneous pin or needle whose tip is intended to contact a point of the subcutaneous anatomical structure or an anatomical structure rigidly connected thereto. An elongated junction member rigidly couples the at least one guiding element to the at least one second contact element.

18 Claims, 14 Drawing Sheets

(51) Int. Cl.
 *A61B 17/00* (2006.01)
 *A61B 17/56* (2006.01)

(52) U.S. Cl.
 CPC ...... *A61B 17/1764* (2013.01); *A61B 17/1775* (2016.11); *A61B 17/1778* (2016.11); *A61B 2017/00526* (2013.01); *A61B 2017/568* (2013.01)

(56) References Cited

U.S. PATENT DOCUMENTS

| | | | |
|---|---|---|---|
| 5,643,272 | A | 7/1997 | Haines et al. |
| 2004/0015173 | A1 | 1/2004 | Irving |
| 2005/0182415 | A1 | 8/2005 | Steffensmeier et al. |
| 2005/0273114 | A1 | 12/2005 | Novak |
| 2008/0114370 | A1* | 5/2008 | Schoenefeld ............ A61F 5/00 606/96 |
| 2008/0119938 | A1 | 5/2008 | Oh |
| 2011/0213376 | A1 | 9/2011 | Maxson et al. |
| 2012/0053594 | A1 | 3/2012 | Pelletier et al. |
| 2012/0215225 | A1 | 8/2012 | Philippon et al. |
| 2014/0074099 | A1 | 3/2014 | Vigneron et al. |
| 2017/0027593 | A1* | 2/2017 | Bojarski ............ A61B 17/1675 |

FOREIGN PATENT DOCUMENTS

| | | | | |
|---|---|---|---|---|
| EP | 2856951 | * | 8/2015 | ............ A61B 17/17 |
| WO | 93/25157 | A1 | 12/1993 | |
| WO | 20121176077 | A1 | 12/2012 | |

OTHER PUBLICATIONS

Invitation to Pay Additional Fees and Partial International Search Report received for PCT Patent Application No. PCT/EP2016/058545, dated Aug. 8, 2016, 8 pages.

International Search Report and Written Opinion received for PCT Patent Application No. PCT/EP2016/058545, dated Oct. 4, 2016, 19 pages.

International Preliminary Report on Patentability received for PCT Patent Application No. PCT/EP2016/058545, dated Oct. 26, 2017, 13 pages.

European Search Report and Written Opinion issued for EP Patent Application No. 15305575.1, dated Nov. 16, 2015, 12 pages.

\* cited by examiner

PATIENT-SPECIFIC SURGICAL GUIDE

FIELD OF THE INVENTION

The invention relates to a patient-specific surgical guide that can be used in orthopedic surgery, such as tibial prosthesis implantation, ankle prosthesis implantation, shoulder prosthesis implantation or high tibial osteotomy.

BACKGROUND OF THE INVENTION

Patient-specific surgical guides become more and more used in orthopedic surgery, for example in view of implanting total knee prosthesis.

A patient-specific guide is generated by an additive manufacturing technique (e.g. stereolithography or selective laser sintering) by including two kinds of elements:

- contact elements intended to match an anatomical structure (e.g. a bone) to be treated; and
- guiding elements such as drill guides, saw guides, or milling guides, intended to guide a surgical instrument in order to treat the anatomical structure in view of implanting the required prosthesis once the patient-specific guide is positioned onto the anatomical structure of the patient.

The planning of the position of the guiding elements is based on the planning of the prosthesis implantation on medical images of the patients such as Computer Tomography (CT), Magnetic Resonance Imaging (MRI), or 3D models built from X-ray projections.

The prosthesis can be a screw, a wedge, a plate, or any articular implant made of several parts, it can be a conventional implant or a patient specific implant made on the basis of medical images of the patient. The planning is performed using a computer. The planning runs a software that calculates all the steps further described for determining geometric positions of pin guides, contact surfaces, milling guides, etc. in relation with the anatomical structures of the patient, for which a surface or volume model is constructed using software and imaging tools.

The contact elements are chosen so as to provide a unique and stable position of the guide with respect to the anatomical structure.

In view of carrying out minimally invasive surgery, the guide should require minimal incisions into the patient's body, while allowing a precise and robust positioning with respect to the anatomical structure to be worked. This is often contradictory. As a result, it is known that state-of-the-art guides often suffer from instability that can lead to inaccuracy of placement of surgical tools. Making them bigger to obtain a larger contact surface for better stability and accuracy goes against the trends for minimally invasive surgery.

BRIEF DESCRIPTION OF THE INVENTION

A goal of the invention is thus to design a patient-specific surgical guide that addresses the above-mentioned problems and in particular that allows a more accurate positioning of the guiding elements, while minimizing the invasiveness of the guide.

The invention provides a patient-specific surgical guide comprising:

- at least one guiding element for guiding a surgical instrument to treat a subcutaneous anatomical structure of the patient, and
- a first patient-specific contact element comprising a first patient-specific contact surface intended to fit a portion of said subcutaneous anatomical structure, said at least one patient-specific contact surface being rigidly connected to the at least one guiding element, said patient-specific surgical guide being characterized in that it further comprises;

- at least one second patient-specific contact element, distant from the first patient-specific contact element, comprising at least one support element suitable for supporting a percutaneous pin or needle whose tip is intended to contact a point of said subcutaneous anatomical structure or of an anatomical structure rigidly connected to said subcutaneous anatomical structure,
- an elongated junction member rigidly coupling said at least one guiding element to the at least one second contact element.

By "anatomical structure" is meant in the present text a substantially rigid subcutaneous structure, such as a bone or cartilage, whose shape can be determined on medical images of the patient and whose shape will not substantially evolve between the acquisition of the medical images and the planning of the surgical intervention. It can be but is not limited to osseous or cartilaginous structures.

By "distant from" is meant that the second patient-specific contact element is arranged relative to the first patient-specific contact element such that the percutaneous pin or needle that is supported by the support element does not pass through the first patient-specific surface. Otherwise said, when the surgical guide is used, the point that is contacted by the percutaneous pin or needle is outside of the portion of the subcutaneous anatomical structure to which the surface of the first patient-specific contact element is fitted. In particular, the second contact element may not necessarily be inserted in the incision through which the first contact element is placed to fit the subcutaneous anatomical structure.

According to an embodiment, the surgical guide further comprises a second patient-specific contact surface intended to match a portion of the patient's skin.

According to an embodiment, said second patient-specific contact surface is integral with the support element.

According to an embodiment, the first patient-specific contact element, the at least one second patient-specific contact element and the guiding element are made by an additive manufacturing technique.

According to an embodiment, the junction member is removable.

Advantageously, the junction member may be a rod having a square cross section.

According to an embodiment, the patient-specific surgical guide comprises a percutaneous pin or needle mounted in a support element of at least one second contact element.

According to an embodiment, said pin or needle is compliantly arranged in the support element so as to allow adjusting orientation and/or position of the pin or needle with respect to said support element.

Another object of the invention is a patient-specific surgical guide for high tibial osteotomy, comprising the features described above, comprising a guiding element configured to guide a saw blade, said guide further comprising at least one of:

- a second contact element having an arch shape intended to extend from a skin portion located above the outer malleolus of the patient to a skin portion located above the inner malleolus of the patient;

a second contact element supporting a pin or needle intended to contact a point of the upper part of the fibula; and a second contact element supporting a pin or needle intended to contact the tibia opposite to the guiding element.

Advantageously, said guide further comprises a guiding element configured for guiding a mill.

According to an embodiment, the guiding element for the saw blade and the guiding element for the mill are removably coupled together to form a modular guiding member.

According to an embodiment, said guide further comprises a patient-specific osteotomy implant having an external part made of a non-porous material and an internal part made of a porous material.

According to an embodiment, the guide comprises four screws intended to be fixed into the anatomical structure, each screw having a spherical head cooperating with the guiding element to attach the guiding element to the anatomical structure.

According to an embodiment, the guide comprises side contact elements rigidly attached to the guiding element for the saw blade and intended to be inserted between the subcutaneous anatomical structure and surrounding soft tissues, said side contact elements comprising a first patient-specific contact surface on the anatomical structure.

Another object of the invention is a surgical guide for shoulder prosthesis implantation, characterized in that it comprises the features described above, wherein the guiding element is configured to guide a drill, said surgical guide comprising at least one second patient-specific contact element supporting a pin or needle adapted to contact a point on the acromion or on the coracoid process of the patient.

Another object of the invention is a surgical guide for tibial prosthesis implantation, characterized in that it comprises the features described above, wherein the guiding element is configured to guide a saw blade, said surgical guide comprising at least two contact elements each supporting a pin or needle adapted to contact the two opposite sides of the sharpest part of the tibial crest of the patient.

Another object of the invention is a surgical guide for ankle prosthesis implantation, characterized in that it comprises the features described above, wherein the guiding element is configured to guide a saw blade, said surgical guide comprising at least two contact elements each supporting a pin or needle adapted to contact the two opposite sides of the sharpest part of the tibial crest of the patient.

Another object of the invention is a method for constructing a patient-specific surgical guide as described above. Said method comprises:

obtaining medical images of the patient containing the anatomical structure to be treated, from said medical images, constructing the first patient-specific contact surface so as to fit a determined portion of said subcutaneous anatomical structure and the at least one guiding element, from said medical images, constructing the second patient-specific contact element such that the tip of each percutaneous pin or needle contacts a determined point of the subcutaneous anatomical structure or of an anatomical structure rigidly connected to said subcutaneous anatomical structure when the first patient-specific contact surface fits the determined portion of the subcutaneous anatomical structure.

According to an embodiment, the method further comprises manufacturing the first patient-specific contact element, the at least one guiding element and the second patient-specific contact element by an additive manufacturing technique.

Another aspect of the invention is a computer program product comprising computer-readable instructions which, when loaded and executed on a suitable system, perform the steps of the method described above.

BRIEF DESCRIPTION OF THE DRAWINGS

Other features and advantages of the invention will be apparent from the appended drawings, wherein.

DETAILED DESCRIPTION OF EMBODIMENTS OF THE INVENTION

Patient-Specific Guide

Figure 1:
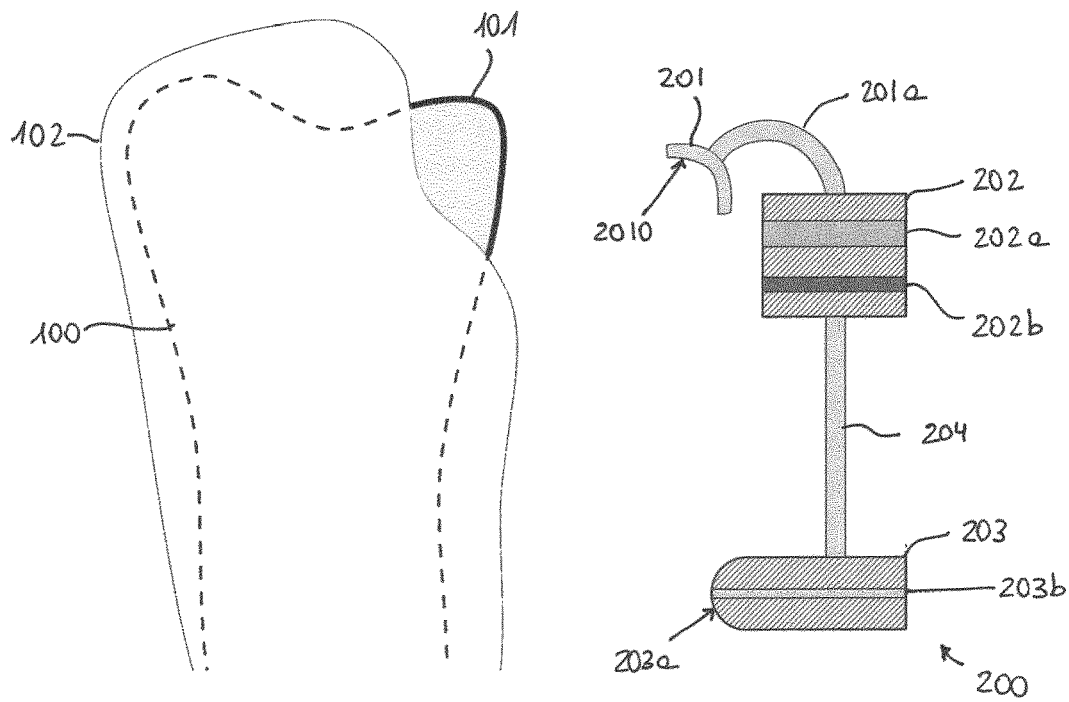
FIGS. 1 and 2 illustrate a patient-specific surgical guide according to an embodiment of the invention, before and during use, respectively.

FIG. 1 shows a patient-specific surgical guide according to an embodiment of the invention along with a body part of the patient onto which it is intended to be secured.

The body part comprises a bone 100 (e.g. a tibia), which comprises bony or cartilaginous area 101 which is accessible to the user via an incision made through the patient's skin 102. The user can be a surgeon, an assistant or a nurse duly habilitated. The bone 100 and area 101 are together referred to as an anatomical structure in the following text.

The patient-specific surgical guide 200 comprises a first patient-specific contact element 201 having a surface 2010 matching a part of the anatomical structure area 101.

The guide 200 further comprises a rigid body 202 comprising at least one guiding element such as a drill guide, a saw guide, and/or a milling guides, intended to guide a respective surgical instrument. The intended position and/or orientation of the guiding element(s) with respect to the anatomical structure is determined previously during a planning procedure performed on medical images of the patient and/or 3D models derived from medical images of the patient.

In the embodiment illustrated in FIG. 1, the rigid body 202 comprises a cutting guide 202a and a drill guide 202b, but this embodiment is only an example and is not intended to be limitative.

In the embodiment shown in FIG. 1, the first contact element 201 is rigidly connected to the rigid body 202 by a junction 201a. In an alternative embodiment, the first contact element may be integrally formed with the rigid body. For example, the first contact element may be located on a face of the rigid body that directly bears onto the anatomical structure. In other words, the surface 2010 can be a part of the rigid body 202 that is directly in contact with the anatomical structure.

Figure 17A:
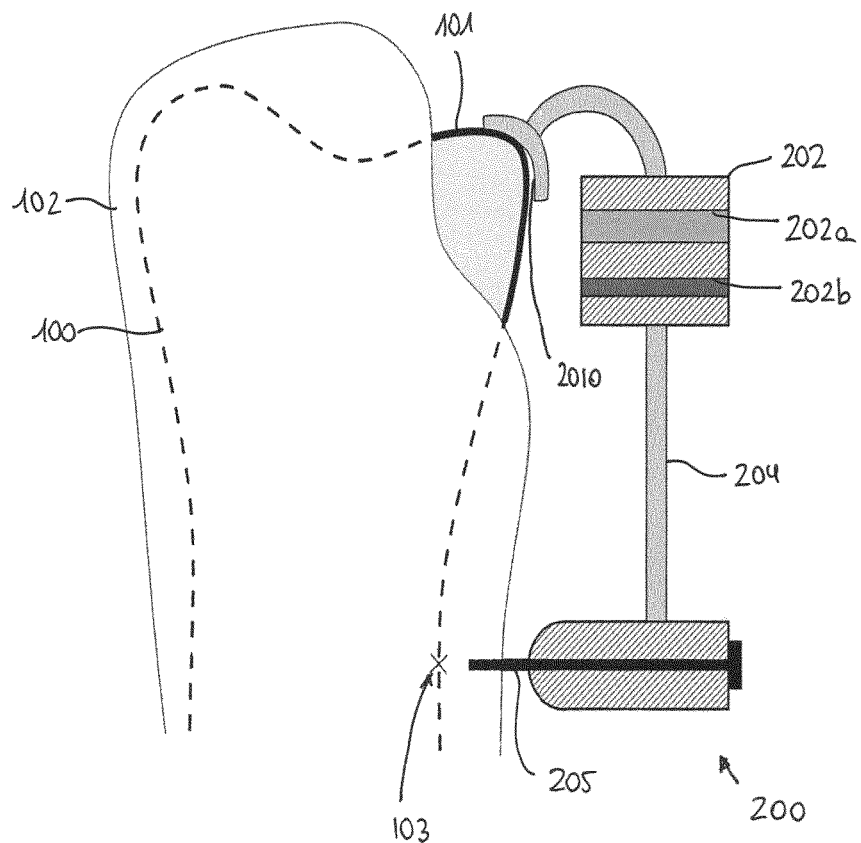
FIGS. 17A-17D illustrate different situations of erroneous positioning of the surgical guide.
Figure 17B:
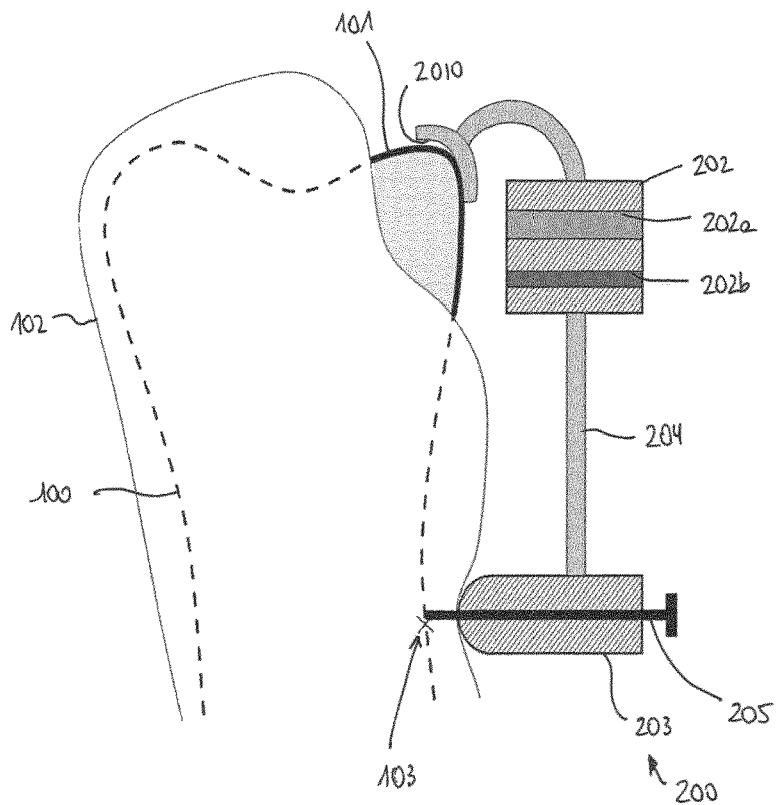
Figure 17C:
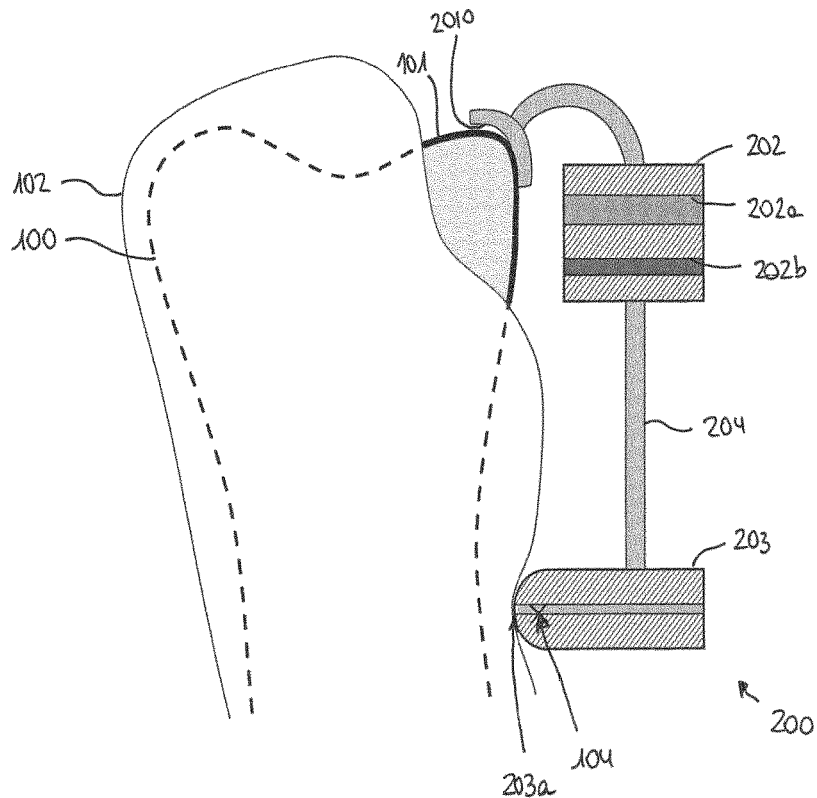
Figure 17D:
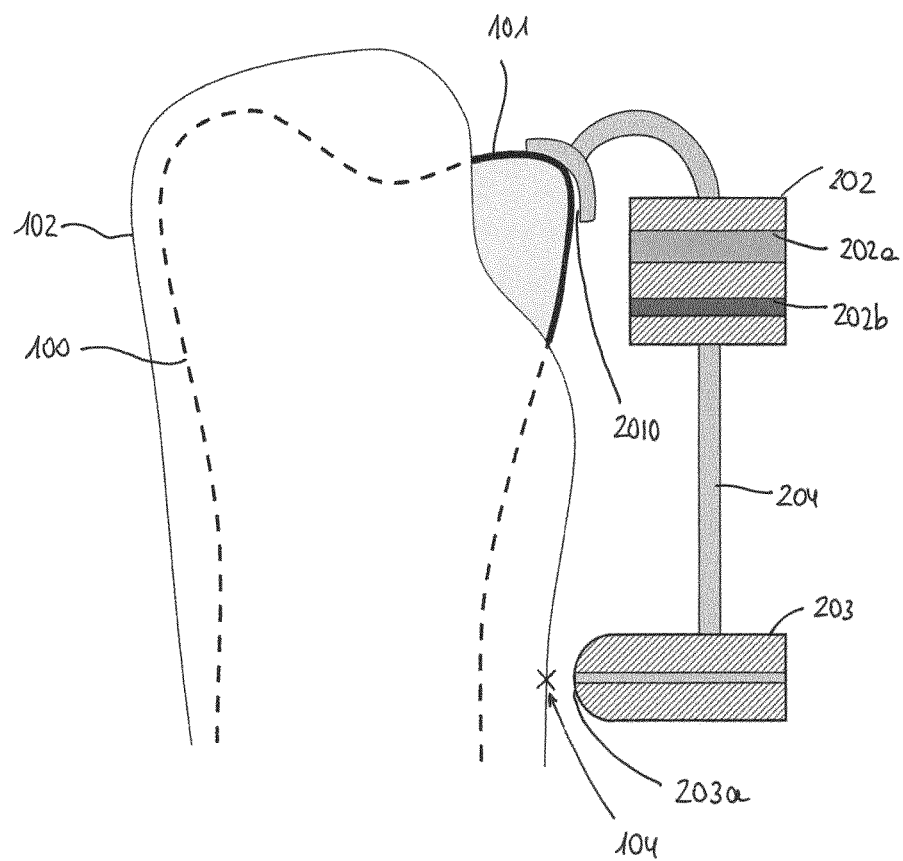

In order to improve the accuracy of the positioning of the rigid body 202, the guide further comprises a second patient-specific contact element 203 that is intended to serve as a guide or support for a pin or needle intended to percutaneously contact an anatomical structure underneath the patient's skin (typically a bone). The second contact element 203 thus comprises a support element 203b which is a hole through which a pin or a needle (not shown) with a given length can be supported. The user may sense whether the pin or needle effectively contacts the anatomical structure at said given length, which shows whether the guide is correctly positioned or not. In addition to the support element 203b, the second contact element 203 may further comprise a contact surface 203a that is intended to bear on the patient's skin. Said second patient-specific contact surface 203a can be integral with the support element 203b or distinct from said support element If the rigid body 202 is not placed as planned, several situations can occur. As shown in FIGS. 17A-17B, the guide 200 is designed such that, in its intended position, the surface 2010 of the first contact element 201 matches a part of the subcutaneous anatomical structure whereas a pin or needle 205 arranged in the second contact element 203 contacts a point 103 located on the subcutaneous anatomical structure. However, the position of the guide is not correct because the surface 2010 does not perfectly match the anatomical structure. This may occur for example when the anatomical structure is substantially flat and does not comprise any feature allowing ensuring a unique positioning of the surface 2010. Such an erroneous positioning may be difficult to see by the user. As shown in FIG. 17A, this erroneous positioning results in the fact that the pin or needle 205 does not contact the planned subcutaneous point 103. This situation is more easily visible by the user, as he can still push the pin or the needle 205 into the soft tissues to contact the planned subcutaneous point 103 despite the fact that the stop of the pin or needle is well positioned against the external tip of second contact element 203. In the situation of FIG. 17B, the pin or needle 205 is not in the correct position relative to the subcutaneous point 103. This situation is more easily visible by the user as this erroneous position is characterized in that the stop of the pin or needle is not positioned against the external tip of second contact element 203. As shown in FIGS. 17C-17D, the guide 200 is designed such that, in its intended position, the surface 2010 of the first contact element 201 matches a part of the subcutaneous anatomical structure whereas the contact surface 203a of the second contact element 203 contacts a region 104 located on the patient's skin. However, the position of the guide is not correct because the surface 2010 does not perfectly match the anatomical structure. This may occur for example when the anatomical structure is substantially flat and does not comprise any feature allowing ensuring a unique positioning of the surface 2010. Such an erroneous positioning may be difficult to see by the user. As shown in FIG. 17C, this wrong positioning results in the fact that the second contact element is pushed too far on the soft tissues, which deforms, evidencing that the contact surface 203a does not contact the skin at the intended region 104. In the situation of FIG. 17D, the contact surface 203a does not contact the intended region 104, which readily informs the user of the wrong positioning. If a needle is not touching the subcutaneous anatomical structure, the guide must be displaced to be pushed towards the subcutaneous anatomical structure in the direction of the needle holder. If a needle is touching the subcutaneous anatomical structure too early before it has reached its targeted position, the guide must be displaced to be pushed backwards the subcutaneous anatomical structure in this direction of the needle holder. With these indications, the user can reposition the guide and check again that the needles and supports are in the desired position.

Advantageously, the second contact element 203 comprises both the contact surface 203a and the support element 203b. Hence, the user is able to decide, during the surgical intervention, whether the contact surface 203a is sufficient to provide a good positioning of the guide 200 (in such case, it is not necessary to insert a pin through hole 203b) or whether the contact surface 203a is not sufficient (in such case, the user inserts a pin through the hole 203b percutaneously, the pin tip being intended to contact the underlying anatomical structure). Such a decision can be made on the basis of patient data and accuracy required. For example if the patient is thin and the skin surface is close to the bone (for example in some areas of the tibial crest), and the patient has not loss or gained significant weight between the medical images acquisition and the surgery, and if no liquid has been injected below the skin in such area, then a user might decide that the contact surface is sufficient.

As compared to a second contact element only intended to bear on the patient's skin, with the support element 203b supporting a pin or a needle, the contact of the pin or needle tip onto the subcutaneous anatomical structure may be more reliable than the sole contact of the contact surface 203a onto the skin. Indeed, during the surgical intervention, the soft tissues may have swelled. As a result, the contact surface 203a may have to be slightly pushed into the soft tissues in order to arrive at the planned position.

According to an embodiment, the pin (or the needle) can be rigidly mounted on the second contact element 203. For example, the pin and the second contact element 203 can consist of a single part. Alternatively, the degrees of freedom of the pin can be blocked by a mechanical mean (e.g. a notch or a clip) on the second contact element 203.

According to an embodiment, the pin (or the needle) can slide within the second contact element 203. A visual indicator can be placed on the second contact element 203 or on the pin to check if the penetration length of the pin coincides with the planned one. Such visual indicator can be a ruler that indicates the potential discrepancy between the desired length of the pin and the actual length. The second contact element 203 can also comprise a stop which will block the translation of the pin, when penetrating the patient's soft tissues. In this case, if the pin (or the needle) connector is not against the stop, it means that the pin did not penetrate soft tissues as planned/expected, and if the pin is against the stop but the user does not feel the contact of the tip with the subcutaneous anatomical structure by pressing the guide towards the skin, it also means that the pin did not penetrate soft tissues as planned/expected.

Figure 15:
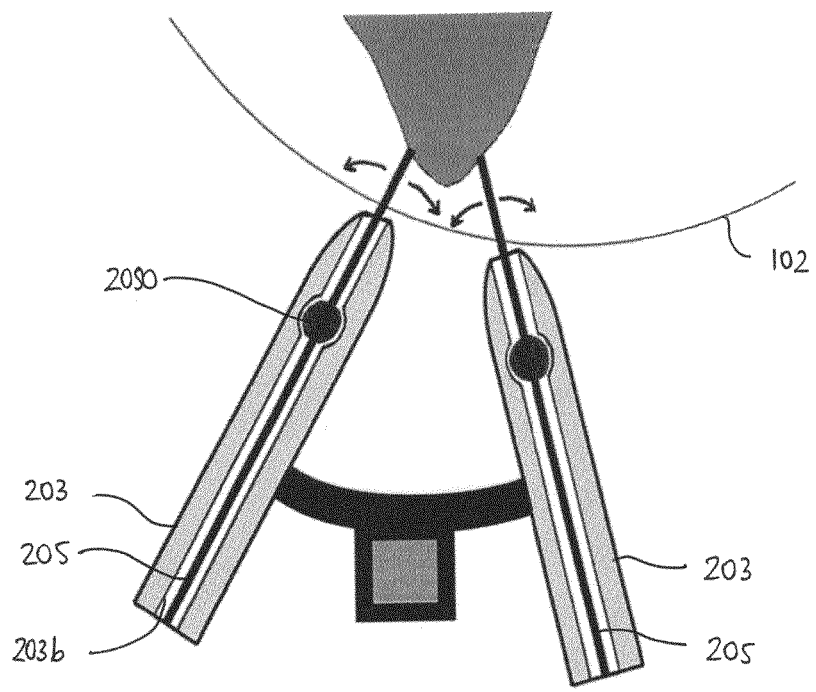
FIG. 15 is a sectional view of a patient-specific surgical guide supporting specific pins or needles and including compliance in terms of positioning and orientation.
Figure 16:
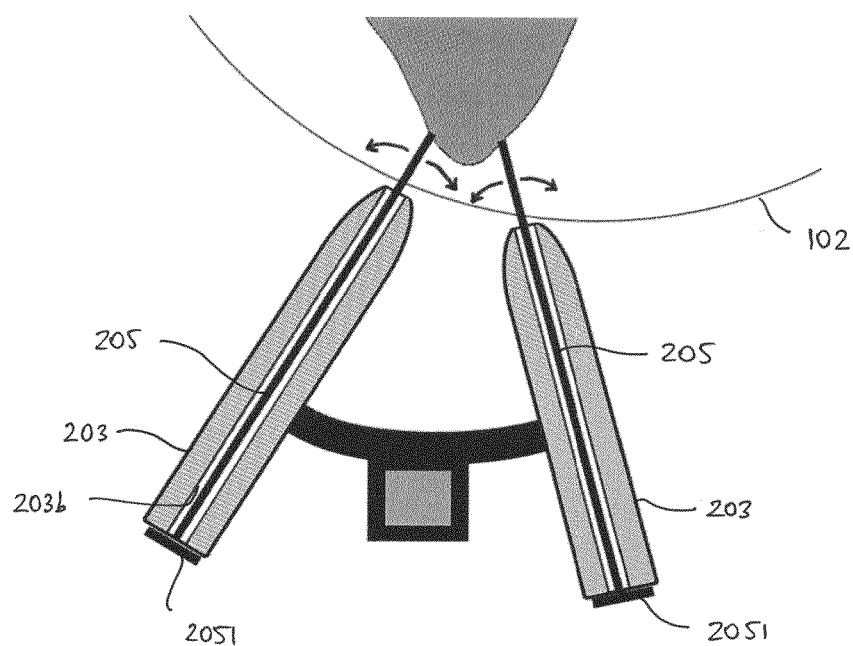
FIG. 16 is a sectional view of a patient-specific surgical guide supporting standard pins or needles and including compliance in terms of positioning and orientation.

According to an embodiment, the pin or the needle can have a predefined compliance in terms of positioning and orientation once placed within the patient's soft tissues (which have hyperelastic mechanical properties), as shown in FIGS. 15 and 16. Indeed, when the user has placed the patient-specific guide 200 and has particularly placed the pins or the needles on the second contact element 203 through the patient's soft tissues (skin 102 for example), the user may realize that the guide does not have the correct positioning on the patient's anatomy. In this case, and as mentioned above, pins or needles are not correctly placed against the subcutaneous anatomical structure or are not in the right position regarding the visual indicators or the stop included in the second contact element 203. As a consequence, the user has two choices. Either pins/needles are removed from the patient's soft tissues and the patient-specific guide 200 can be placed again, or the user can try to find the right position of the patient-specific guide 200 by adjusting the positioning of the second contact element 203 and particularly the pin (or needle) positioning/orientation within this element and within the soft tissues of the patient, without removing the needles/pins from the patient which has the advantage to be less invasive and save time.

It is possible to introduce a low compliance into the second contact element 203 regarding the needle orientation because the error which will be made is not significant considering the large distance (e.g. large lever arm) between the rigid body 202 and the second contact element 203. Moreover, the positioning of the rigid body 202 and the first contact element 201 is never very far from the correct planned positioning, even when the user places the guide 200 for the first time on the patient's anatomy.

To introduce compliance to the pin (or the needle) when mounted into the second contact element 203, two solutions are possible.

In the embodiment shown in FIG. 15, a specific pin 205 (or a specific needle) comprising a spherical part 2050 can be mounted within the guiding element 203b of the second contact element 203, the guiding element having an inner diameter slightly greater than the outer diameter of the pin or needle. In this case, the orientation of the pin can be slightly modified, around the sphere center, as shown by the arrows. This deviation can be computed and consequently mastered to avoid large errors. In other words, the guiding element 203b of the second contact element can be designed to limit the compliance to an acceptable range.

In the embodiment shown in FIG. 16, the pin 205 is straight but has an end connector 2051. The guiding element 203b in which the pin 205 (or the needle) is placed can have a diameter slightly larger than the diameter of the pin (or the needle). In this case, the pin (or the needle) will be able to twist slightly (as shown by the arrows) and find a correct position, especially if the connector 2051 of the pin or needle is maintained and fixed into the second contact element 203. The error which is made is not significant and the difference in terms of pin (or needle) length is very limited compared to the distance between the rigid body 202 and the second contact element 203. Furthermore, the diameter of the guiding element 203b can be computed to limit the compliance to an acceptable range.

If compliance has been included in the system, it is also preferable to place a large number of pins or needles through a large number of second contact elements to make the guide 200 as stable as possible.

Preferably, the surface 2010 of the first contact element 201 is designed to fit an area of the anatomical structure that has a feature such as a non-planar shape, in order to provide a unique stable position of the guide with respect to the anatomical structure and thus to minimize a positioning error of the guide.

In addition, the surface 2010 should be as close as possible to the planned cutting plane or drilling axis, in order to minimize the invasiveness of the guide.

Although only one first contact element 201 with one surface 2010 is shown in FIG. 1, the surgical guide could comprise a greater number of first contact elements or of contact surfaces directly pertaining to the rigid body comprising the guiding element(s).

By contrast, the second contact element 203, which does not require any incision to be positioned on the patient, can be located at a certain distance from the cutting plane or drilling axis. This allows taking advantage of a body portion that offers features allowing a better positioning, even if it is farther from the region to be treated. Depending on the application, the anatomical structure contacted by the second contact element may be the same as the anatomical structure to be treated (e.g. when the anatomical structure to be treated is an elongated bone such as a tibia, both the first and second patient-specific contact elements can contact the same anatomical structure) or another anatomical structure adjacent to the anatomical structure to be treated and rigidly coupled to it (e.g. when the anatomical structure to be treated is a tibia, the second anatomical structure may be the fibula). For example, in the applications described below, there may be a distance of several tenth centimeters between the first patient-specific contact surface and at least one second patient-specific contact element.

The second contact element 203 is rigidly connected to the rigid body 202 by an elongated junction member 204.

According to an embodiment, the junction member 204 is a rod that is removable from the rigid body 202 and/or the second contact element 203.

According to a preferred embodiment, the rod 204 has a square cross section. In this way, the rod allows blocking a degree of freedom in rotation of the second contact element with respect to the rigid body 202.

According to an embodiment, the rod 204 is manufactured with a length specific to the patient. Otherwise, the rod may be provided with a given length, and the parts of the rigid body and the second contact element that are intended to be connected to the rod have a patient-specific design in order to ensure a determined distance between the rigid body and the second contact element. According to an embodiment, the rod can be provided in different lengths (e.g. small, medium and large) depending on the patient's size, and the surgical guide is provided to the user with an indication as to the rod length that has to be used. The same mark is used on the rod and on the parts of the rigid body and second element. In the above-described embodiments, the rod can be connected to the rigid body and the second contact element in a unique manner, so that the user can be sure of the correct relative positioning of the rigid body and the second contact element. For example, the rod may be clipped into the rigid body and the second contact element. Various types of clip mechanism can be used.

Alternatively, the rod may be provided with a plurality of graduations, and the surgical guide is provided to the user with an indication as to the graduation that has to be used for the patient. This allows using a unique rod regardless of the treated patient.

Although only one second contact element 203 is shown in FIG. 1, the surgical guide could comprise a greater number of second contact elements. In such case, one or some second contact elements may be coupled to the rigid body by a removable rod as described above, whereas one or some other second contact elements may be coupled to the rigid body by a fixed junction.

Figure 2:
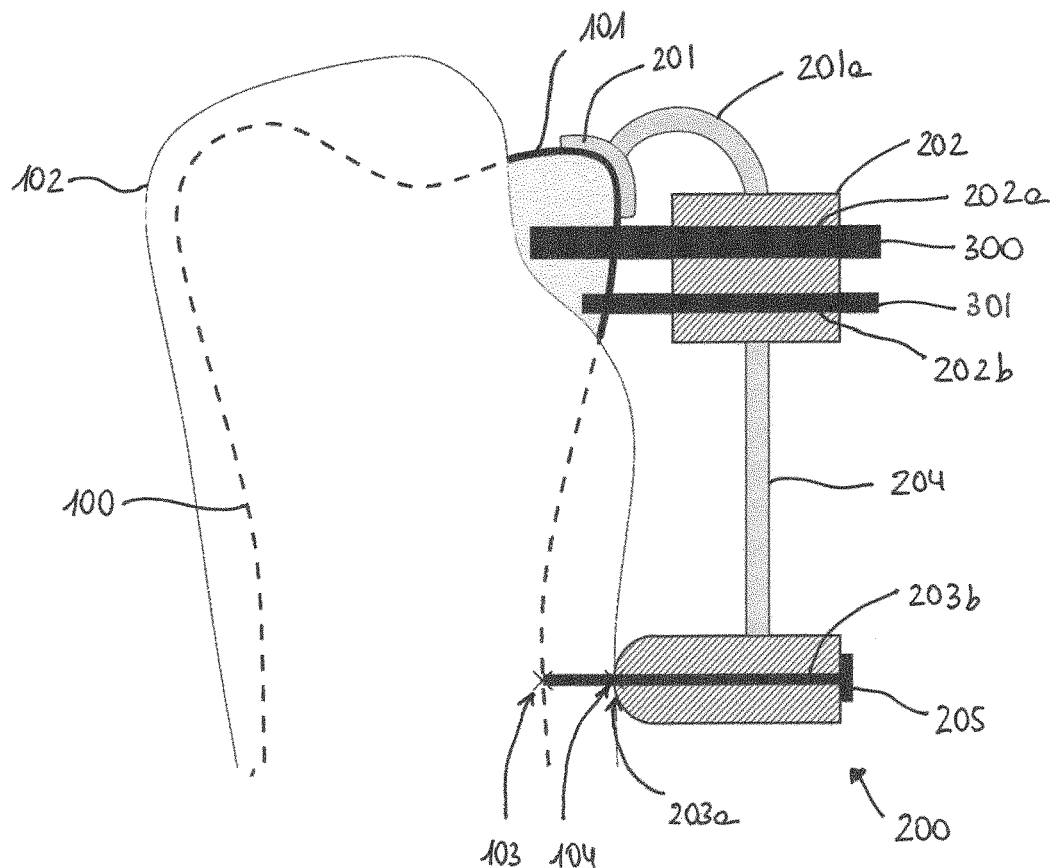

FIG. 2 shows the patient-specific guide of FIG. 1 once positioned on the anatomical structure of the patient.

If required, a pin or a needle 205 can be inserted through the guiding element 203b until a subcutaneous contact point 103 on the anatomical structure. This may be useful in particular if there is a large thickness of soft tissues such as flesh and/or fat between the skin and the anatomical structure. The length of the pin or needle to be inserted percutaneously is patient-specific and is determined during planning and construction of the surgical guide.

Figure 13:
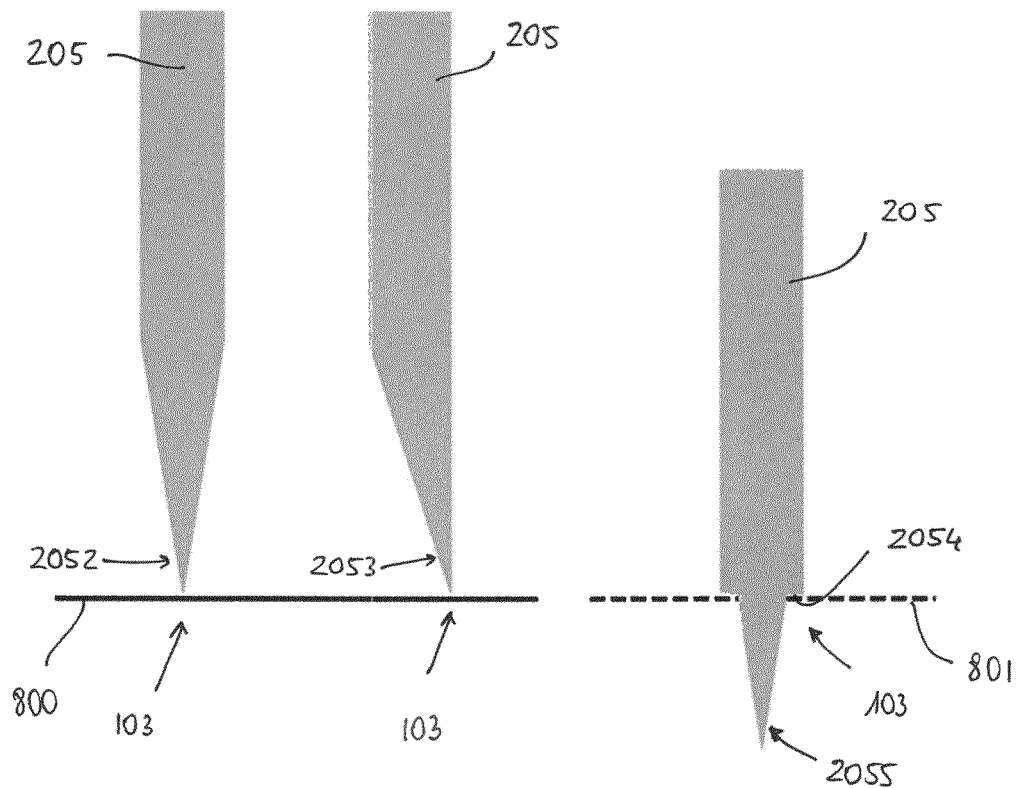
FIG. 13 illustrates various embodiments of the pin or needle tips.

The tip of the pin or the needle 205 can have different shapes, some of them being depicted in FIG. 13, but are not limited to these shapes.

If the contact point 103 has been planned on a high density subcutaneous anatomical surface 800, the pin or the needle tip can be very sharp (e.g. central-pointed tip 2052 or beveled-pointed tip 2053). The penetration of the tip in the subcutaneous anatomical structure will be negligible and will not cause a large error (the largest the distance between the rigid body 202 and the second contact element 203, the largest the lever arm, the smallest the error).

If the planned contact point 103 has been planned on a subcutaneous anatomical surface 801 with lower density, the pin or the needle tip may comprise a stop 2054 which will be positioned against the surface of the subcutaneous anatomical structure 801. In contrast, the sharpest part of the pin or the needle tip 2055 will penetrate the subcutaneous anatomical structure 801. The sharpest part of the pin is optional and a large enough diameter of the needle can be also sufficient to create a stop.

Otherwise, the contact between the contact surface 203a and a cutaneous contact point or surface 104 is sufficient to provide a good positioning of the guide. This may be the case in particular if there is a small thickness of soft tissues between the skin and the anatomical structure.

The rigid body 202 of the guide 200 can thus be firmly secured to the anatomical structure, e.g. using pins or screws (not shown).

Then, a saw blade 300 can be inserted in the saw guide 202a in order to cut the anatomical structure along a planned cutting plane, and/or a drill 301 can be inserted in the drill guide 202b to drill the anatomical structure along a planned drilling axis.

The construction of the rigid body 202 and the first contact element 201 is a well-known process which has been previously described in a number of patents and which is not in the scope of this invention, unlike the construction of the second contact element 203 that will be described below.

Several features of the second contact element 203 must be initially set: its contact points or surfaces, its orientation and its length. The rest of the second contact element design (e.g. connectors to bind the multiple second contact elements 203 that have been designed and support elements to be mounted on the rod 204) is finally deduced from the planned position of the rigid body 202 and from the above mentioned features.

Contact points or surfaces can be directly defined on the anatomical structures which are visible on 3D medical images (e.g. CT or MRI) of the patient. Anatomical structures can be bone, cartilage or skin for example, but are not limited to these structures.

In particular, the contact surface 203a of the second contact element 203 can be constructed by selecting a contact point 104 or a contact surface on the patient's skin which is visible and easily detectable on medical images of the patient.

The orientation of the second contact element 203 can be adjusted to be normal to the targeted anatomical surface, or as close as possible to this normal vector, for example. It is also possible to define a max threshold such as thirty degrees between the pin axis and the normal vector to guarantee to obtain a stable constraint.

The length of the second contact element 203 can be determined from the initial length of the pin (or the needle) or can be adjusted to a given length if the pin (or the needle) does not have a fixed length. In the case of a pin (or a needle) with a fixed length, the second contact element length can be directly obtained by computing the difference between the pin (or needle) initial length and the total penetration distance of the pin (or the needle) through the soft tissues until reaching the subcutaneous contact point 103 which can be directly selected on the 3D medical images of the patient, on the bone boarder or cartilage boarder for example.

According to an embodiment, the subcutaneous contact point 103 can be preferably selected on hard cortical bone to avoid penetration of pin or needle during its insertion. The selection of this point can be optimized by analyzing the Hounsfield Units which are directly related to bone density in the patient's medical images if CT images are used (the larger the Hounsfield Unit, the denser the bone).

All patient-specific parts of the guide can be made by additive manufacturing.

Use of the patient-specific guide will now be described in connection with four possible applications, namely implantation of a tibial prosthesis, implantation of an ankle prosthesis, implantation of a shoulder prosthesis and high tibial osteotomy. However, the invention is not limited to these applications and a patient-specific guide as described above could be designed and used in other surgical applications without departing from the scope of the invention.

Tibial Prosthesis Implantation

Knee prosthesis implantation can be necessary when a patient suffers from knee osteoarthritis. The knee prosthesis generally comprises a femoral prosthesis, a tibial insert and a tibial prosthesis. Patient-specific guides can be used by the user to perform the implantation of the two prostheses. The present application is focused on tibial prosthesis implantation.

Current tibial patient-specific guides are sometimes described as inaccurate, particularly when setting the tibial slope. It can be due to soft tissues which are located near the tibial plateaus, below the contact areas of the tibial patient-specific guide, and which are not sufficiently cleaned up by the user. Moreover, the user has no mean sufficiently accurate to check tibial guide positioning preoperatively.

Figure 11:
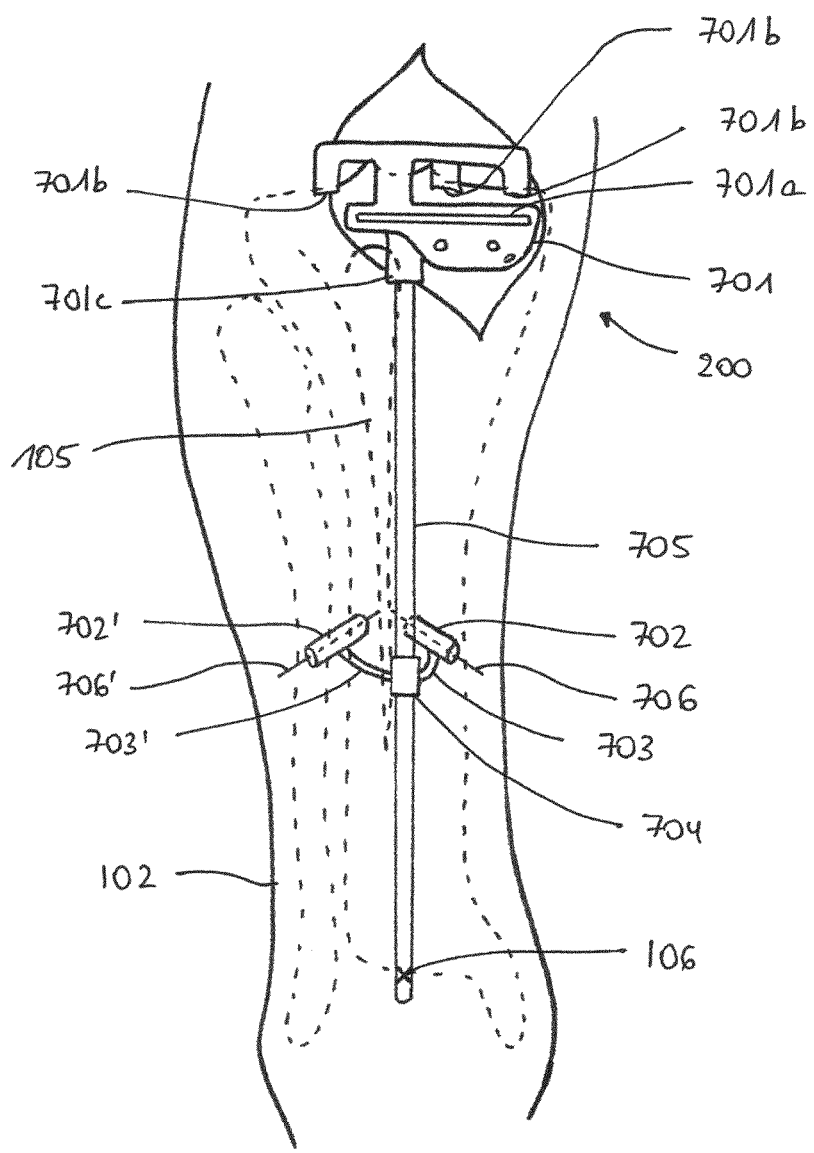
FIG. 11 illustrates a patient-specific surgical guide according to an embodiment of the invention, dedicated to tibial prosthesis implantation.

FIG. 11 illustrates an embodiment of a patient-specific guide 200 intended for tibial prosthesis implantation.

The guide comprises a rigid body 701 comprising a slot-shaped guiding element 701a for guiding a saw blade. The rigid body 701 can be firmly secured to the anatomical structure thanks to three holes using pins or screws (not shown). The number of holes dedicated to guide fastening can vary.

The rigid body 701 has several surfaces 701b matching the anatomical structure to be cut.

Two second contact elements 702, 702' are provided in order to more accurately position the surgical guide 200 with respect to the anatomical structure.

Figure 12:
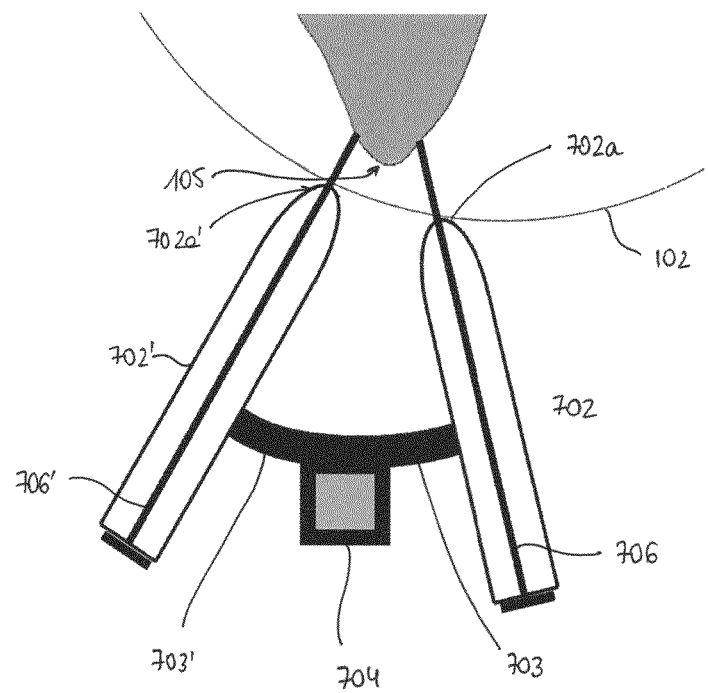
FIG. 12 is a sectional view of a part of the patient-specific surgical guide of FIG. 11 in a plane perpendicular to the tibial long axis and located in the sharpest part of the tibial crest.

The second contact elements 702, 702' each comprise a through hole for supporting a needle or a pin 706 intended to contact the two opposite sides of the sharpest part of the tibial crest 105 as shown in FIG. 12.

The second contact elements 702, 702' are rigidly coupled to a support 704 by respective junctions 703, 703'. The support 704 is mounted on a rod 705, preferably having a square cross section as described above.

The rigid body 701 is also rigidly coupled to the rod 705, by the means of a support 701c which is rigidly coupled to the rigid body 701.

According to an embodiment, the rod 705 can be graduated or can be provided in different lengths as described above.

According to an embodiment, the rod 705 can be aligned with the ankle center 106. This alignment is a visual reference that helps the user positioning the guide 200 once assembled.

In the embodiment illustrated in FIG. 11, the second contact elements 702, 702' are not designed to bear on the patient's skin and thus do not comprise any patient-specific skin contact surface. Only the patient-specific orientation of the through holes with respect to the cutting plane, and the length of the respective pins, are taken into account in the construction of the guide 200. In an alternative embodiment illustrated in FIG. 12, the second contact element 702 and/or the second contact element 702' may also be provided with a patient-specific surface 702a, 702a' intended to match a portion of the patient's skin 102. Indeed, the location on the tibial crest is advantageous for placing patient-specific surface on patient's skin as the skin is quite thin in this region of the tibia.

The more second contact elements, the more accurate the positioning. However, it should be understood that only one of the second contact elements 702, 702' could be implemented without departing from the scope of the present invention.

Ankle Prosthesis Implantation

To treat patients suffering from ankle osteoarthritis, the user can perform an ankle prosthesis implantation. The implantation of such a prosthesis is not trivial for the user and requires a lot of complex conventional instruments. Thus, patient-specific guides can be an interesting solution for helping the user to perform this complex surgical procedure. An ankle prosthesis generally consists of an implant placed on the distal extremity of the tibia, an implant on the talus and an insert which is placed between the two implants. The present application is focused on the implant that is placed on the distal tibia.

Figure 14:
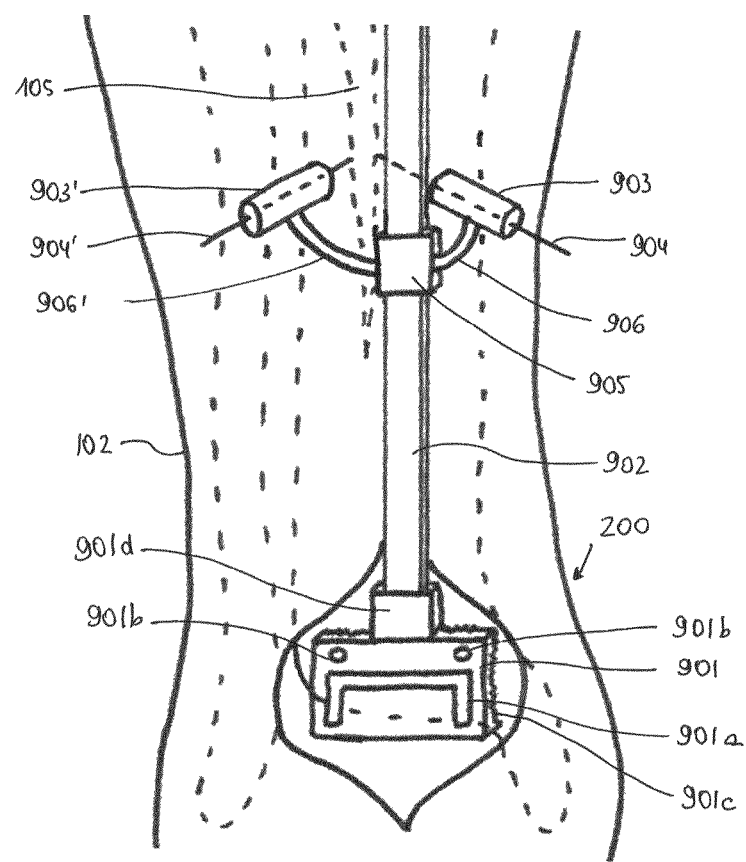
FIG. 14 illustrates a patient-specific surgical guide according to an embodiment of the invention, dedicated to ankle prosthesis implantation.

FIG. 14 illustrates an embodiment of a patient-specific guide 200 intended for ankle prosthesis implantation, especially for the distal tibial implant.

The guide comprises a rigid body 901 comprising a slot-shaped guiding element 901a for guiding a saw blade. The rigid body 901 can be firmly secured to the anatomical structure thanks to a pair of holes 901b using pins or screws (not shown). The number of holes dedicated to guide fastening can vary.

The rigid body 901 has a surface 901c matching the anatomical structure to be cut. In this sense, the rigid body is integral with the first contact element.

Since the anatomical structure is substantially flat in the internal region of the distal tibia that is to be cut, the first contact element may not ensure alone a precise positioning of the guide.

Two second contact elements 903, 903' are provided in order to more accurately position the surgical guide 200 with respect to the anatomical structure.

The second contact elements 903, 903' each comprise a through hole for supporting a needle or a pin 904, 904' intended to contact the two opposite sides of the sharpest part of the tibial crest 105 in a similar way as in FIG. 12.

The second contact elements 903, 903' are rigidly coupled to a support 905 by respective junctions 906, 906'. The support 905 is mounted on a rod 902, preferably having a square cross section as described above.

Figure 3:
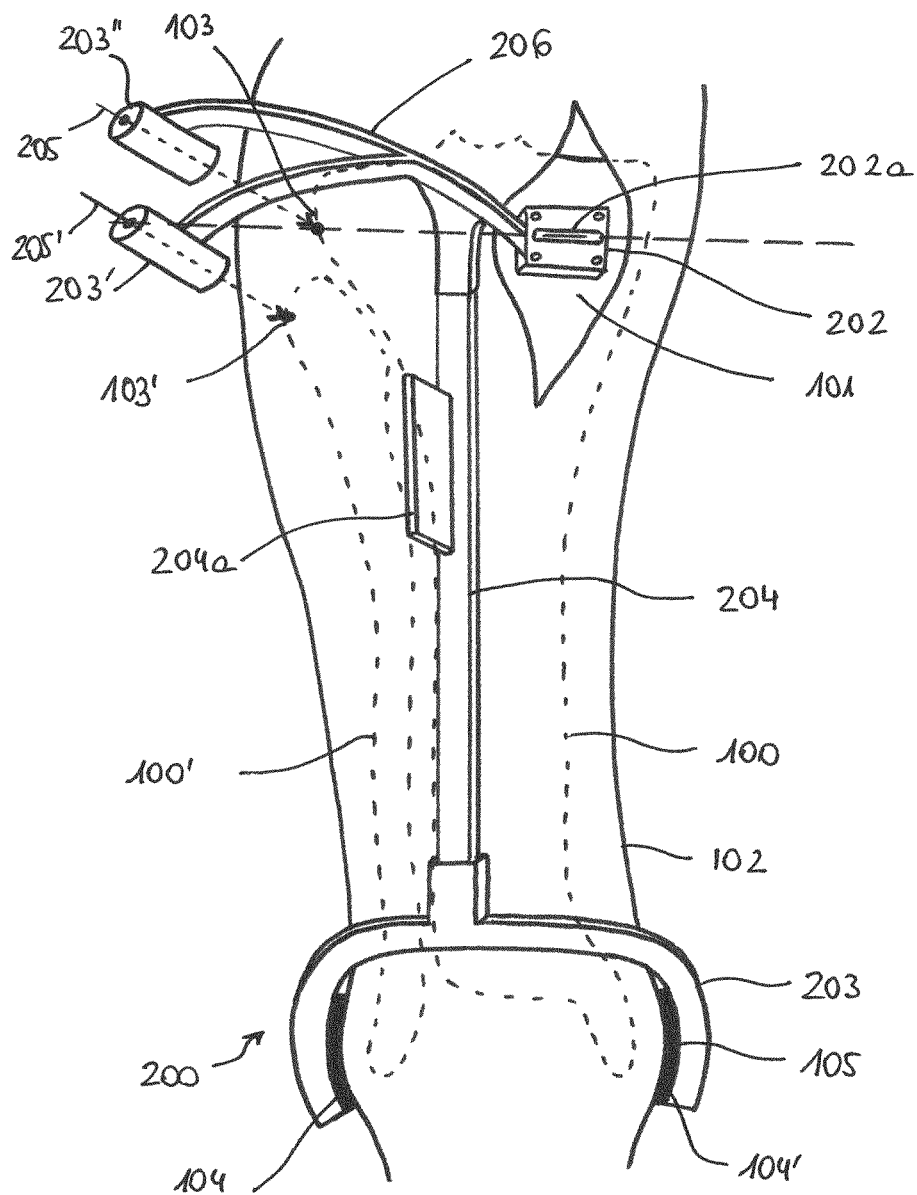
FIG. 3 illustrates a patient-specific surgical guide according to an embodiment of the invention, dedicated to high tibial osteotomy.

According to an embodiment, an additional second contact element could be an arch extending from a skin portion located above the outer malleolus to a skin portion located above the inner malleolus of the patient as described in FIG. 3 (but not shown in FIG. 14), the surface of the second contact element being patient-specific.

The rigid body 901 is also rigidly coupled to the rod 902, by the means of a support 901d which is rigidly coupled to the rigid body 901.

According to an embodiment, the rod 902 can be graduated or can be provided in different lengths as described above.

According to an embodiment, the rod 902 can be aligned with the ankle center. This alignment is a visual reference that helps the user positioning the guide 200 once assembled.

In the embodiment illustrated in FIG. 14, the second contact elements 903, 903' are not designed to bear on the patient's skin and thus do not comprise any patient-specific skin contact surface. Only the patient-specific orientation of the through holes with respect to the cutting plane, and the length of the respective pins, are taken into account in the construction of the guide 200. In another embodiment (similar as FIG. 12), the second contact element 903 and/or the second contact element 903' may also be provided with a patient-specific surface intended to match a portion of the patient's skin 102. Indeed, the location on the tibial crest is advantageous for placing patient-specific surface on patient's skin as the skin is quite thin in this region of the tibia.

The more second contact elements, the more accurate the positioning. However, it should be understood that only one of the second contact elements 903, 903' could be implemented without departing from the scope of the present invention.

Shoulder Prosthesis Implantation

Shoulder prosthesis is a well-known solution to treat patients suffering from shoulder osteoarthritis. The implantation of such a prosthesis is not very accurate as the conventional surgical instrumentation is not based usually on palpable anatomical references because the incision that is performed by the user in the patient's shoulder is very small. As a consequence, the use of the surgical instruments is consequently quite approximate.

Thus, patient-specific drilling guides can be a very interesting solution for helping the user to perform this complex surgical procedure in a very accurate manner. As the access to the anatomical portion to be treated is very limited, the positioning of the drilling patient-specific surgical guide can be cumbersome, quite approximate if not inaccurate. Thus, additional contact elements could be useful to find the correct position of the patient-specific guide.

According to an embodiment, the rigid body of the patient specific guide comprising the drill channel can be coupled rigidly with at least one second contact element. This second contact element is provided in order to more accurately position the surgical guide with respect to the anatomical structure. The second contact element comprises a through hole for supporting a needle or a pin intended to contact a part of a subcutaneous anatomical structure of the shoulder that is not accessible via the incision. This subcutaneous anatomical structure can be but is not limited to a portion of the acromion or a portion of the coracoid process.

In order to improve the accuracy of the positioning of the patient-specific drilling guide, the guide further comprises a second patient-specific contact element that is intended to either contact the patient's skin or to serve as a support for a pin intended to percutaneously contact an anatomical structure underneath the patient's skin, as described above.

The more second contact elements, the more accurate the positioning. However, it should be understood that only one of the second contact elements could be implemented without departing from the scope of the present invention.

High Tibial Osteotomy

Tibial osteotomy is an important technique for treating knee osteoarthritis. In essence, tibial osteotomy is intended to adjust the geometry of the knee joint so as to transfer weight bearing load from arthritic portions of the joint to relatively unaffected portions of the joint.

Open wedge osteotomy consists in making a partial cut into the upper portion of the tibia so as to create a hinge, manipulating the tibia so as to open a wedge-like opening in the bone, and then securing the bone in this position by inserting a wedge-shaped implant into the opening in the bone or an external plate with screws, whereby to reorient the lower portion of the tibia relative to the tibial plateau and hence adjust the manner in which load is transferred from the femur to the tibia.

While this technique provides substantial benefits to the patient, it is procedurally challenging for the user. In particular, it can be difficult to create the wedge-like opening in the bone with the necessary precision and with a minimum of trauma to the surrounding tissue (e.g. the neurological and vascular structures at the back of the knee).

FIG. 3 illustrates an embodiment of a patient-specific guide 200 intended for high tibial osteotomy.

The guide comprises a rigid body 202 comprising a slot-shaped guiding element 202*a* for guiding a saw blade.

The rigid body 202 has a surface matching the anatomical structure to be cut. In this sense, the rigid body is integral with the first contact element.

Since the anatomical structure is substantially flat in the internal region of the upper tibia that is to be cut, the first contact element may not ensure alone a precise positioning of the guide.

Three second contact elements 203, 203', 203" are provided in order to more accurately position the surgical guide 200 with respect to the anatomical structure.

The second contact element 203 has an arch shape extending from a skin portion 104 located above the outer malleolus to a skin portion 104' located above the inner malleolus of the patient. The surface of the second contact element 203 contacting a respective skin portion 104, 104' is patient-specific in order to fit it. Advantageously, the construction of the second contact element 203 takes into account an additional thickness to the skin in order to compensate the fact that during the surgical intervention, a thin band 105 is usually wrapped around the patient's ankle.

The arch-shaped second contact element 203 is rigidly coupled to the rigid body 202 by a rod 204, preferably having a square cross section as described above. According to an embodiment, the rod 204 comprises a rib 204*a* extending in the sagittal plane of the patient's tibia. This rib 204*a* forms a visual reference that helps the user positioning the guide 200 once assembled.

The guide 200 further comprises a second contact element 203" that comprises a through hole for supporting a needle or a pin 205 intended to contact the tibia opposite the cut. Advantageously, the contact point 103 for said needle or pin 205 is a point of the surface of the bone, at the level of the hinge. In particular this contact point can be the summit of the bony hinge. Indeed, this point can be quite easily identified by the user and used for double check of the cutting plane. Other contact points can be used in addition or in substitution of this particular point.

In addition to or instead of the second contact element 203', the guide 200 may comprise another second contact element 203' that comprises a through hole for supporting a needle or a pin 205' intended to contact a point 103' of the upper part of the fibula 100'. Indeed, this part of the fibula can be quite easily identified by the user. This point has the advantage that it will help to fix the translation of the device along an axis parallel to the long axis of the tibia.

The second contact elements 203', 203" are rigidly coupled to the rigid body by respective junctions. In the case illustrated in FIG. 3, one Y-shaped junction 206 is used to couple in a non-removable way the rigid body 202 to both second contact elements 203', 203". However, the skilled person could select other types of junctions, whether removable or not, without departing from the scope of the present invention.

In the embodiment illustrated in FIG. 3, the second contact elements 203', 203" are not designed to bear on the patient's skin and thus do not comprise any patient-specific skin contact surface. Only the patient-specific orientation of the through holes with respect to the cutting plane, and the length of the respective pins, are taken into account in the construction of the guide 200. In another embodiment (not shown), the second contact element 203' and/or the second contact element 203" may also be provided with a patient-specific surface intended to match a portion of the patient's skin.

The more second contact elements, the more accurate the positioning. However, it should be understood that only one or two of the second contact elements 203, 203', 203" could be implemented without departing from the scope of the present invention.

Remarkably, a small error (e.g. 2 or 3 mm) in the positioning of the rigid body 202 along the tibial long axis will have very little impact since the opening will reach the desired value. Only the wedge depth will be impacted and consequently erroneous by about 1 or 2 mm only.

Figure 4:
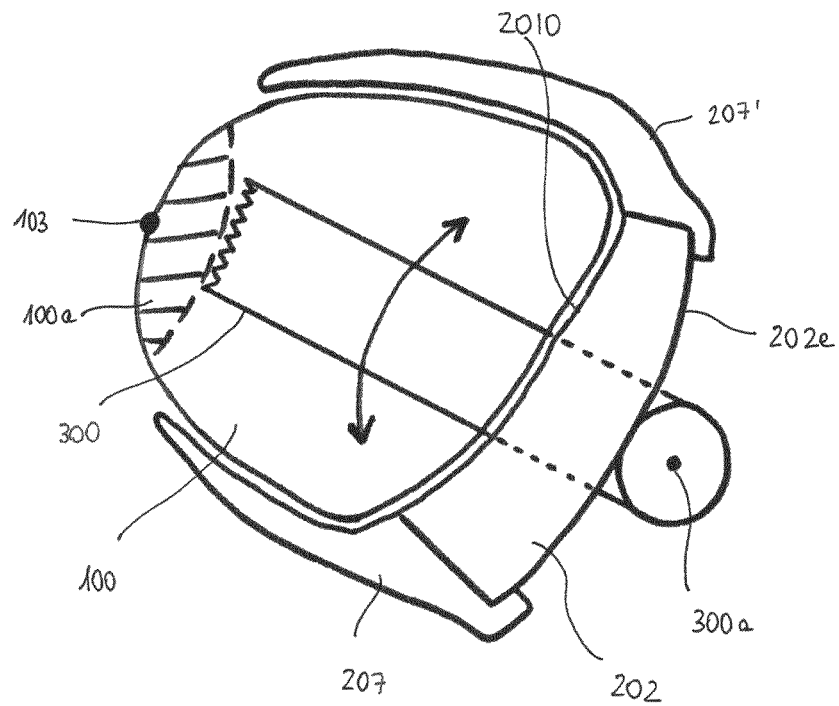
FIG. 4 is a sectional view of the patient-specific surgical guide of FIG. 3 along the cutting plane.

As can be seen better in FIG. 4, the edge 202e around the slot 202a of the rigid body 202 is intended to support a saw blade 300, which oscillates around its center of rotation 300a and slides along the edge 202e. This edge is used as a stop of the center of rotation of the oscillating saw blade. The shape of said surface 202e is patient-specific and thus determines the planned shape of the hinge 100a that is created in the bone 100. To visualize the hinge for a given edge 202e, the saw blade virtually slides around the edge 202e and virtually rotates for each point. The tip of the saw blade is made of teeth that are approximated by a line segment, for an oscillation this gives a circular arc. For all positions along the edge 202e, the circular arcs are computed and merged. The result gives the maximum cut that can be performed, which therefore protects the hinge from being too small and break. It is then the responsibility of the user to ensure that he passed the sawblade sufficiently in order to get enough bone cut to be able to open the bone.

Point 103 corresponds to the summit of the bony hinge 100a, i.e. the point corresponding to the greater thickness of the hinge.

According to an embodiment, the contact surface between the surgical guide and the anatomical structure can be further increased by attaching to the rigid body side contact elements 207, 207' extending along the anatomical structure toward the hinge. These contact elements are also patient-specific and are placed between the bone and the surrounding soft tissues. These contact elements allow both protecting surrounding soft tissues from being cut during the use of the saw blade and increasing significantly the contact surface all around the bone.

Figure 5A:
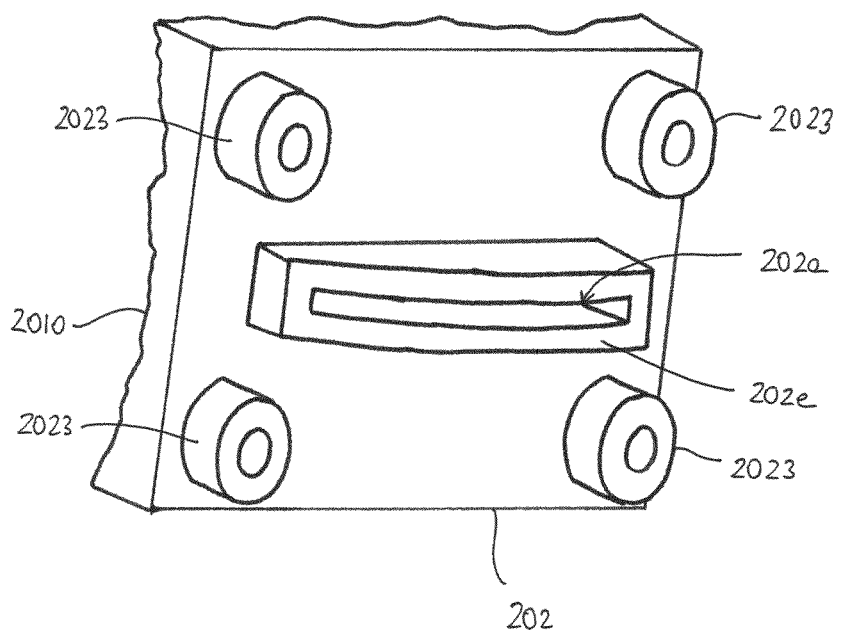
FIG. 5A is a perspective view of the cutting guide of FIG. 4.

FIG. 5A is a perspective view of the rigid body 202.

On either side of the slot 202a, the rigid body comprises two pairs of through holes delimited by circumferential flanges 2023 that are intended to receive pins or screws intended to secure the rigid body to the anatomical structure when the cut is being performed. The number of holes dedicated to guide fastening can vary.

Figure 5B:
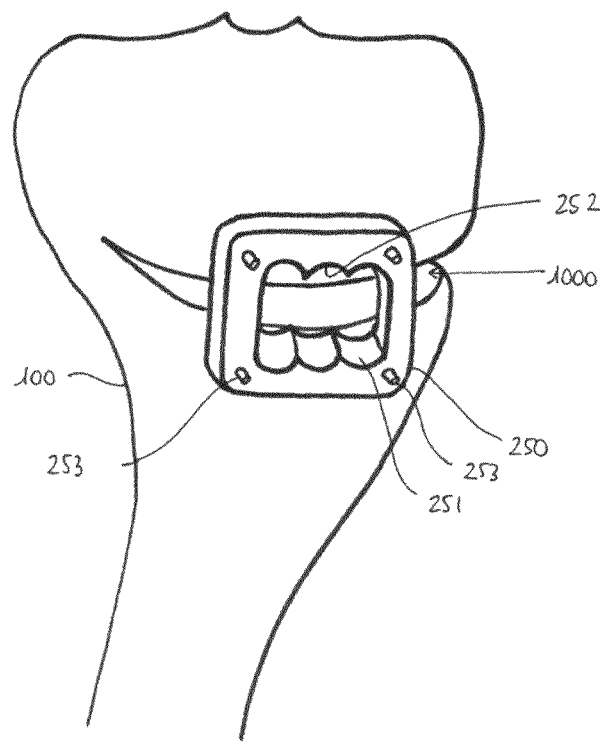
FIG. 5B is a perspective view of a milling guide that can be secured to the anatomical structure after removal of the cutting guide.
Figure 5C:
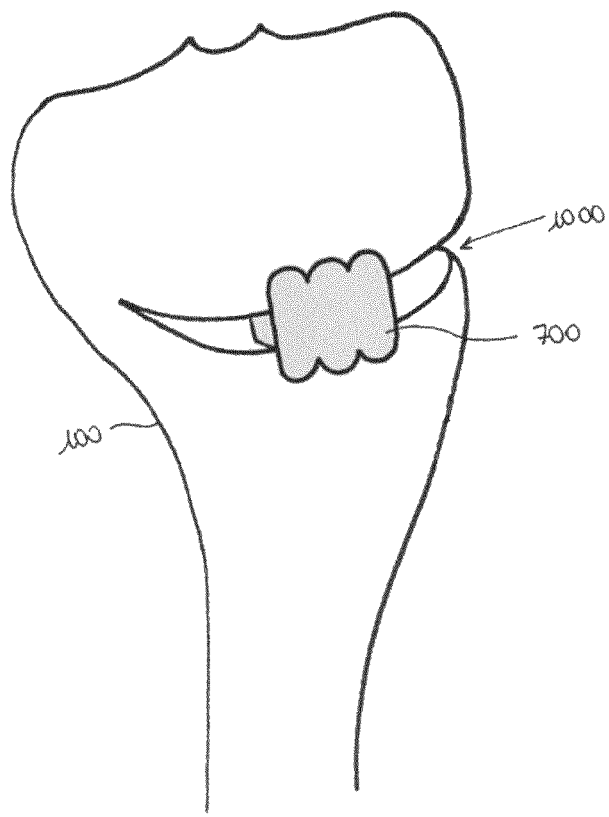
FIG. 5C is a perspective view of a high tibial osteotomy implant implanted into the anatomical structure after milling and removal of the milling guide.

FIG. 5B is a perspective view of a milling guide 250 that can be secured to the anatomical structure 100, 101 with pins or screws 253 and used to carry out the milling which is required to place the implant using the guiding surfaces 251, 252. Since the relative orientation of the pins or screws 253 may have changed after cutting and/or distraction of the anatomical structure, the milling guide may be secured with only a pair of screws on one side of the cutting plane. The implant can then be placed in the milled area, as shown in FIG. 5C. This milling guide is designed for each patient to coincide with the screw heads for a desired position of the opening wedge.

Figure 6A:
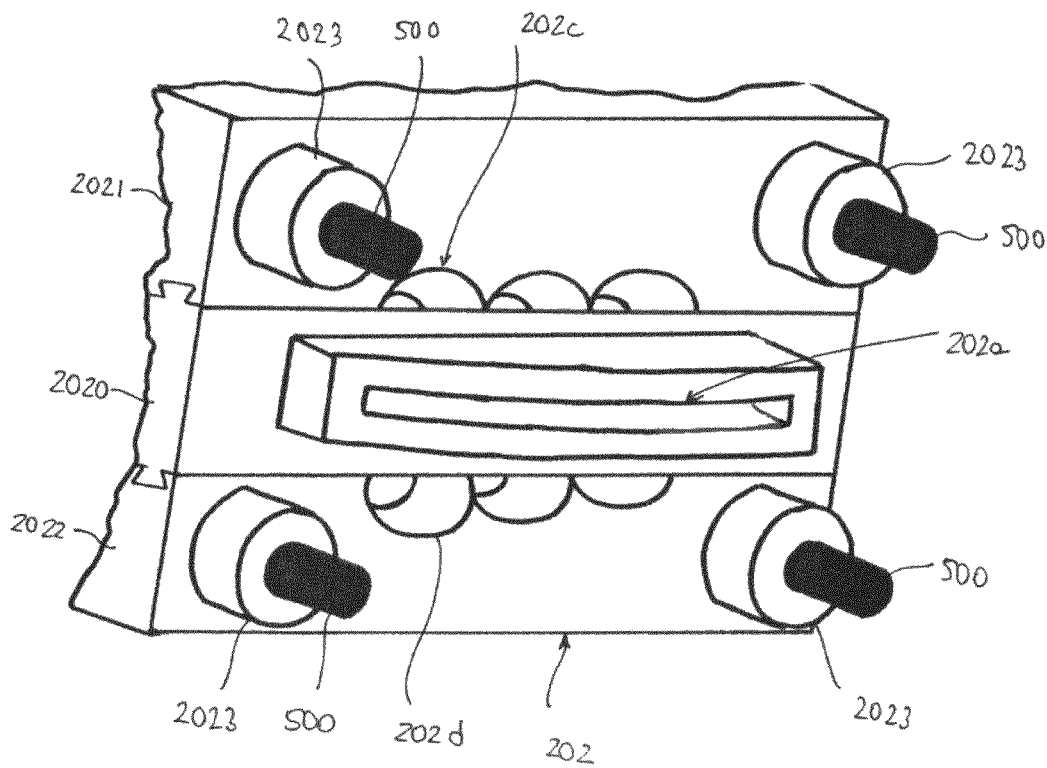
FIG. 6A is a perspective view of a modular surgical guide comprising both a cutting guide and a milling guide coupled together.

FIG. 6A shows an alternative embodiment of the rigid body 202.

In this embodiment, the milling guide and cutting guide are coupled in a removable way, the slot 202a being made in a central part 2020 and the milling guide being split into two parts 2021, 2022 on either side of the central part 2020. The coupling between part 2020 and parts 2021, 2022 is for example of the dovetail type, although any other type of coupling could be used.

In view of positioning and securing the guide to the anatomical structure, the parts 2020-2022 are provided in an assembled state, as shown in FIG. 6A. Then, the user may carry out the cut using the slot 202a.

Figure 6B:
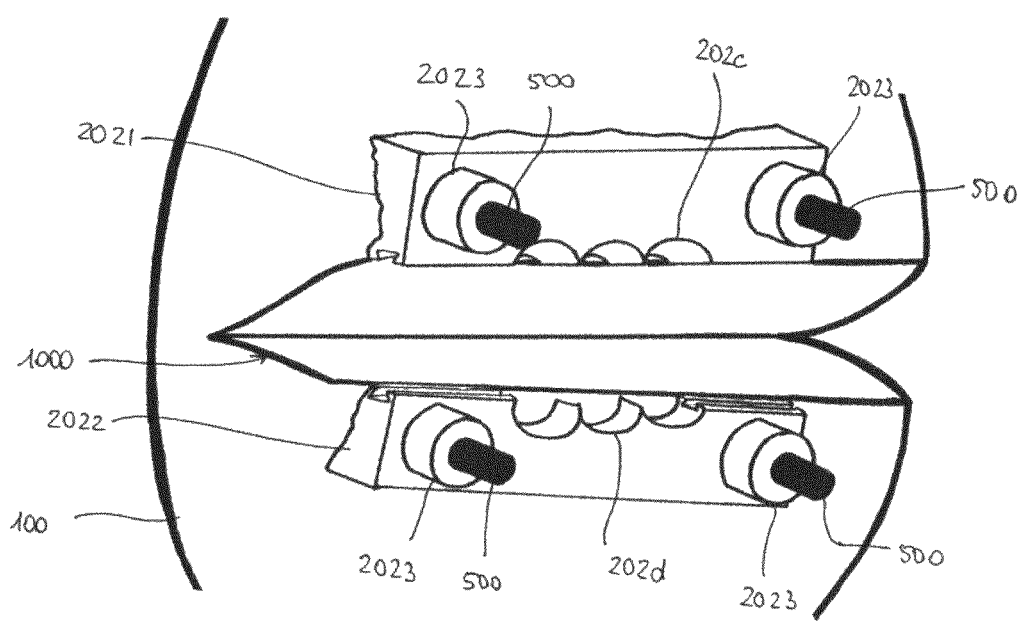
FIG. 6B is a perspective view of the surgical guide of FIG. 6A after removal of the cutting guide.

Once the cut 1000 has been performed, the central part 2020 is removed, as shown in FIG. 6B. Then, the user may carry out the required milling using the guiding surfaces 202c, 202d. The milling shape is designed using a computer software at the planning stage such that when the wedge is opened at the desired value, the implant will naturally fit with the milled part of the bone.

Figure 7A:
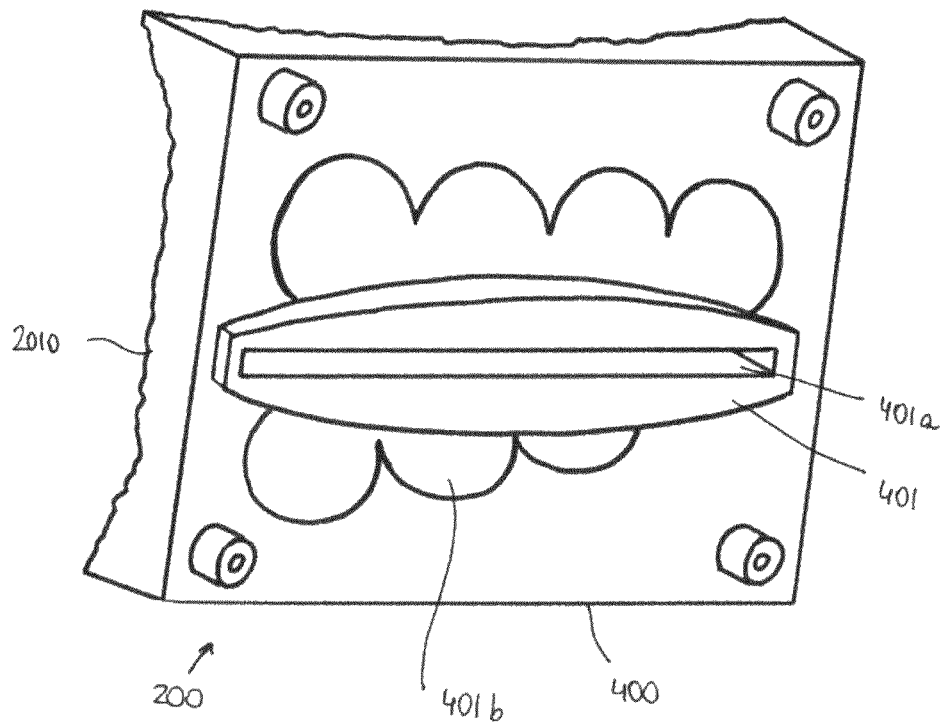
FIG. 7A is a perspective view of a modular surgical guide comprising both a cutting guide and a milling guide that can be disassembled.

FIG. 7A shows an alternative embodiment of the rigid body 202.

In this embodiment, the milling guide and cutting guide are coupled in a removable way. The central element 401 comprising the slot 401a and a volume complementary to the milling surface 401b can be disassembled from the milling element 400. The coupling between part 400 and part 401 is for example of the dovetail type (as shown in FIG. 7A, surfaces 400a and 401b are very close to each other, taking into account a certain assembly clearance), although any other type of coupling could be used.

Figure 7B:
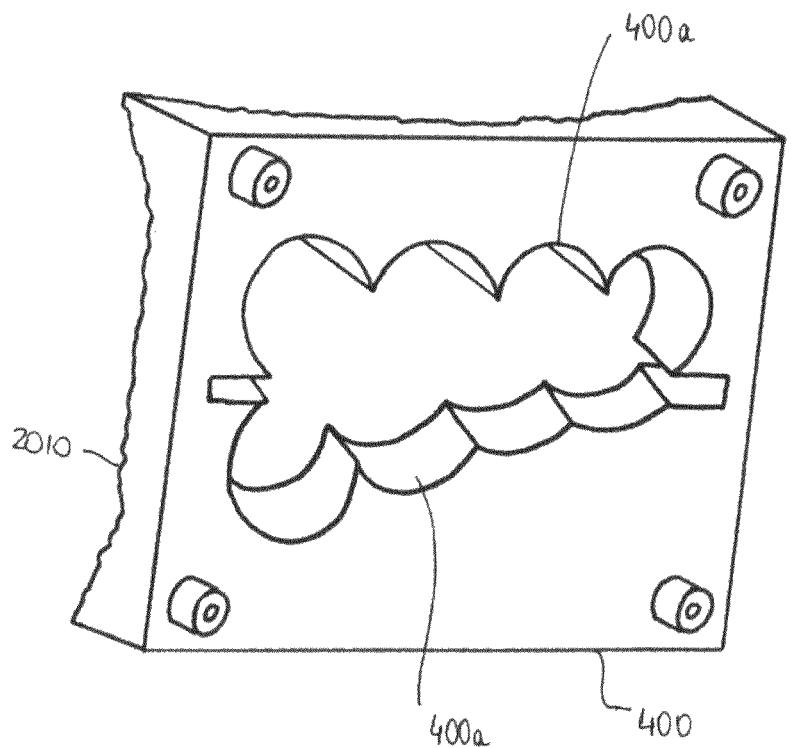
FIG. 7B is a perspective view of the surgical guide of FIG. 7A after removal of the cutting guide. It is another technical solution to be able to perform both cutting and milling operations with the same guide (alternative to the modular surgical guide of FIGS. 6A and 6B)

Considering the assembly shown in FIG. 7A, the user can perform either the cut first or the milling first. Indeed, the shape of the milling surface 400a is determined during the planning process considering the planned osteotomy opening angle. The milling shape is designed using a computer software at the planning stage such that when the wedge is virtually opened at the desired value, the implant will naturally fit with the milled part of the bone. So virtually, in the planning software, the cut is made, the wedge is opened to the desired value, the implant cavity is milled for that opened position, then the wedge is virtually closed back and the milling shape is defined for that closed position before opening If the cut is performed first through the cutting slot 401a, element 401 is then removed from element 400, as shown in FIG. 7B, and the user can carry out the milling using the guiding surface 400a. If the milling is performed first using the guiding surface 400a of element 400, element 401 is then positioned univocally on element 400 and the user can carry out the cut using the cutting slot 401a.

The distraction of the bony parts on either sides of the cut can be carried out before or after the milling step.

Then, an osteotomy implant having a shape complementary to the milled surfaces can be inserted in the opening, and secured to the anatomical surface, as shown in FIG. 5C.

Figure 9:
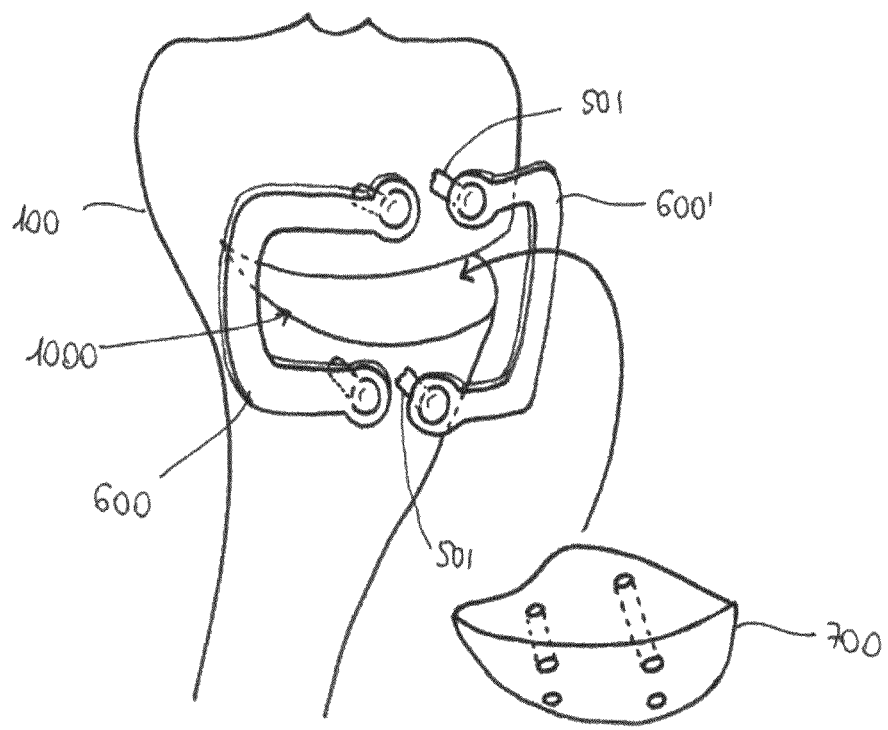
FIG. 9 illustrates distractors mounted on the pins of FIGS. 8A-8B together with a patient-specific osteotomy implant that can be used to fill the created gap.
Figure 10:
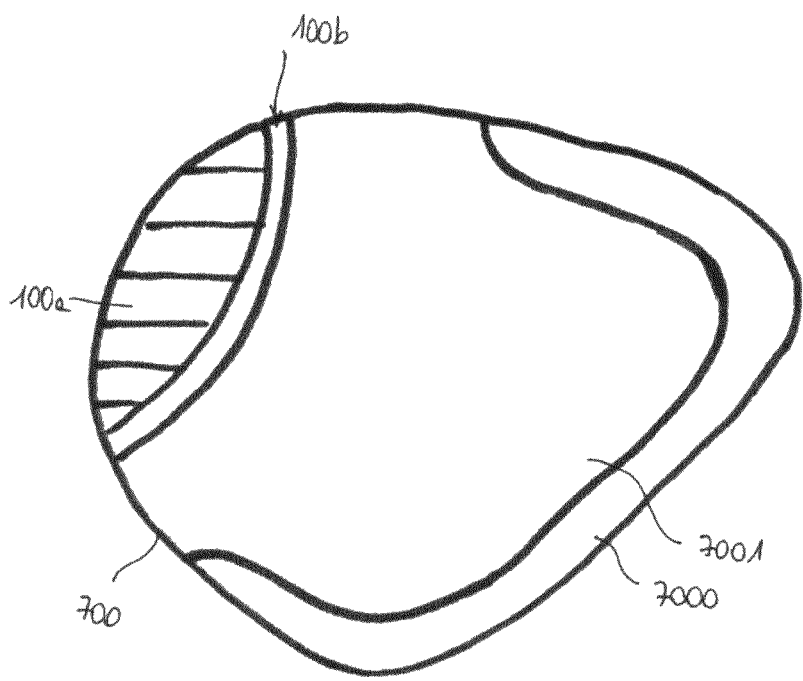
FIG. 10 illustrates, in sectional view, the structure of the patient-specific implant of FIG. 9 mounted in the opening created in the tibia.

According to an embodiment, the implant may be patient-specific, as shown in FIGS. 9 and 10. This allows ensuring that the implant 700 is inserted until a certain distance from the hinge 100a, while leaving a clearance area 100b between the implant and the hinge in order not to have a very sharp and fragile edge. Alternatively, the implant may be a standard one, possibly provided with a limited number of different sizes and/or shapes, the most suitable size and/or shape depending on the patient being selected by the user during the planning phase, and this choice can be reconsidered during surgery to take into account unexpected events.

According to an embodiment, the implant 700 is a patient-specific implant that may comprise an external part 7000 made of a hard, non-porous material, and an inner part 7001 which is porous in order to promote osteo-integration.

Having a perfectly fitted cortical support on the edge of the implant increases the stability of the tibia immediately after surgery which makes it possible to have a faster recovery for the patient.

According to an embodiment, prior to carrying out osteotomy, pins are implanted into the tibia so as to subsequently allow securing a patient-specific cutting guide, a distractor and/or a milling guide.

Figure 8A:
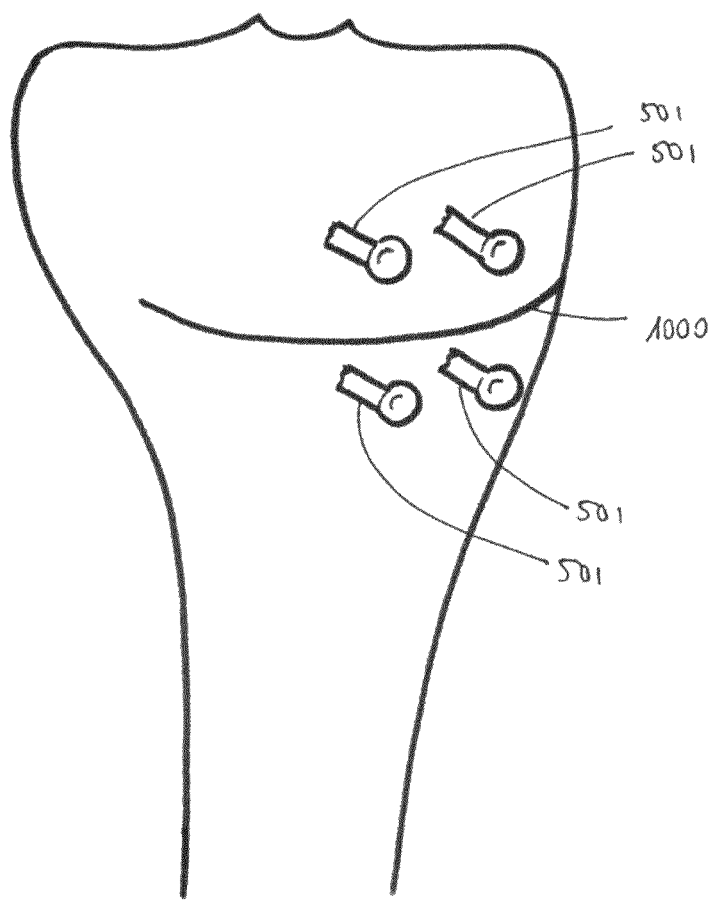
FIGS. 8A and 8B illustrate in perspective and sectional views pins that may be used to secure a cutting guide, a distractor and/or a milling guide to the anatomical structure.
Figure 8B:
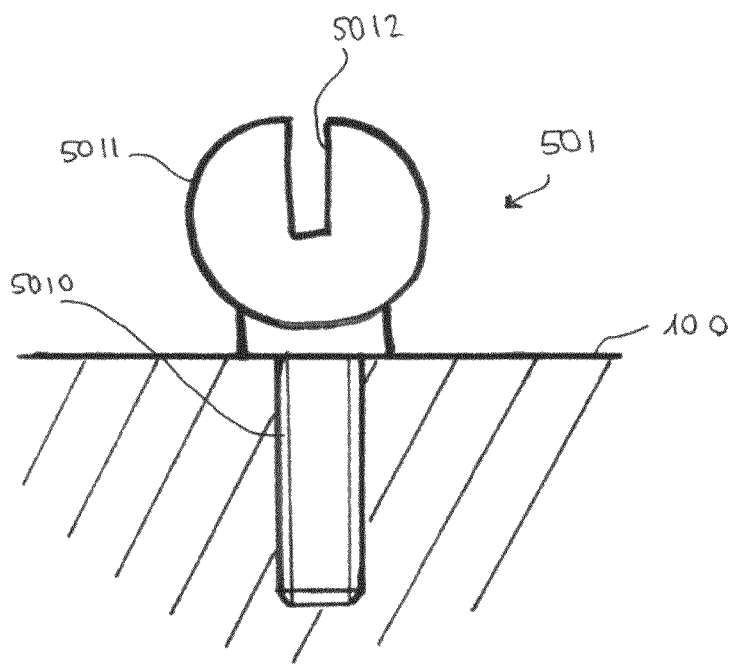

For example, as shown in FIG. 8A, two pins 501 are positioned above the intended cutting plane 1000 and two pins are positioned below said plane, the pins 501 being arranged at the apices of a rectangle. As better shown in FIG. 8B, the pins 501 are provided with a spherical head 5011 that is intended to be coupled to respective fixation means provided on the cutting guide, the distractor and/or the milling guide. Due to this spherical coupling, fixation of the cutting guide, distractor and milling guide remains possible on the same pins although the orientation of the pins is modified after distraction of the anatomical structure.

Advantageously, the spherical head 5011 also serves as a screw head with a dedicated slot 5012 or any other shape that can cooperate with a screwdriver. In this way, a threaded portion 5010 of the pin can be screwed into the bone 100.

FIG. 9 illustrates the positioning of distractors 600, 600' each on two pins 501 on either side of the cutting plane 1000. Once the bone 100 is distracted in the desired configuration, the patient-specific implant 700 can be inserted in the opening.

The invention claimed is:

1. A patient-specific surgical guide comprising:
   at least one guiding element configured for guiding a surgical cutting instrument to treat a subcutaneous anatomical structure of the patient, and
   a first patient-specific contact element comprising a contact surface configured to fit a portion of said subcutaneous anatomical structure, said contact surface being rigidly connected to the at least one guiding element, the contact surface being configured to be in contact with the anatomical structure during cutting of the anatomical structure by a surgical cutting instrument guided by the at least one guiding element,
   at least one second patient-specific contact element distant from the first patient-specific contact element, comprising
   a second patient-specific contact surface configured to match a portion of the patient's skin, and
   at least one support element configured to support a percutaneous pin or needle, wherein the tip of the percutaneous pin or needle is configured to abut said subcutaneous anatomical structure or an anatomical structure rigidly connected to said subcutaneous anatomical structure, wherein the support element comprises a through hole configured for passing the percutaneous pin or needle through the second patient-specific contact surface,
   an elongated junction member rigidly coupling the at least one guiding element to the at least one second contact element.

2. The patient-specific surgical guide of claim 1, wherein said second patient-specific contact surface is integral with the support element.

3. The patient-specific surgical guide of claim 1, wherein the first patient-specific contact element, the at least one second patient-specific contact element and the guiding element are made by an additive manufacturing technique.

4. The patient-specific surgical guide of claim 1, wherein the junction member is removable.

5. The patient-specific surgical guide of claim 1, wherein the junction member is a rod having a square cross section.

6. The patient-specific surgical guide of claim 1, further comprising a percutaneous pin or needle mounted in a support element of a respective second contact element.

7. The patient-specific surgical guide according to claim 6, wherein the percutaneous pin or needle is compliantly arranged in the support element so as to allow adjusting orientation and/or position of the percutaneous pin or needle with respect to said support element.

8. The patient-specific surgical guide of claim 1 for high tibial osteotomy, comprising a first guiding element configured to guide a saw blade, the patient-specific surgical guide further comprising at least one of:
   a second contact element having an arch shape configured to extend from a skin portion located above the outer malleolus of the patient to a skin portion located above the inner malleolus of the patient;
   a second contact element supporting a pin or needle intended to contact a point of the upper part of the fibula; and
   a second contact element supporting a pin or needle intended to contact the tibia opposite the guiding element.

9. The patient-specific surgical guide according to claim 8, further comprising a second guiding element configured for guiding a mill.

10. The patient-specific surgical guide according to claim 9, wherein the first guiding element and the second guiding element are removably coupled together to form a modular guiding member.

11. The patient-specific surgical guide of claim 8, further comprising a patient-specific osteotomy implant having an external part made of a non-porous material and an internal part made of a porous material.

12. The patient-specific surgical guide of claim 8, further comprising four screws configured to be fixed into the anatomical structure, each screw having a spherical head cooperating with the first guiding element to attach the first guiding element to the anatomical structure.

13. The patient-specific surgical guide of claim 8, further comprising side contact elements rigidly attached to the first guiding element and configured to be inserted between the subcutaneous anatomical structure and surrounding soft tissues, said side contact elements comprising a first patient-specific contact surface on the anatomical structure.

14. The patient-specific surgical guide of claim 1 for shoulder prosthesis implantation, wherein the guiding element is configured to guide a drill, said patient-specific surgical guide comprising at least one second patient-specific contact element supporting a pin or needle adapted to contact a point on the acromion or on the coracoid process of the patient.

15. The patient-specific surgical guide of claim 1 for tibial prosthesis implantation, wherein the guiding element is configured to guide a saw blade, said patient-specific surgical guide comprising at least two contact elements each supporting a pin or needle adapted to contact two opposite sides of a sharpest part of a tibial crest of the patient.

16. The patient-specific surgical guide of claim 1 for ankle prosthesis implantation, wherein the guiding element is configured to guide a saw blade, said patient-specific surgical guide comprising at least two contact elements each supporting a pin or needle adapted to contact two opposite sides of a sharpest part of a tibial crest of the patient.

17. A method for constructing a patient-specific surgical guide according to claim 1, comprising:

obtaining medical images of the patient containing the anatomical structure to be treated, from said medical images, constructing the first patient-specific contact surface so as to fit a determined portion of said subcutaneous anatomical structure and the at least one guiding element, and constructing the second patient-specific contact surface so as to fit a determined portion of the patient's skin, and from said medical images, constructing the second patient-specific contact element such that the tip of each percutaneous pin or needle contacts a determined point of the subcutaneous anatomical structure or of an anatomical structure rigidly connected to said subcutaneous anatomical structure when the first patient-specific contact surface fits the determined portion of the subcutaneous anatomical structure.

18. The method according to claim 17, further comprising manufacturing the first patient-specific contact element, the at least one guiding element and the second patient-specific contact element by an additive manufacturing technique.

* * * * *